US008798342B2

(12) United States Patent
Perrey et al.

(10) Patent No.: US 8,798,342 B2
(45) Date of Patent: Aug. 5, 2014

(54) METHOD AND SYSTEM FOR ULTRASOUND IMAGING WITH CROSS-PLANE IMAGES

(75) Inventors: Christian Fritz Perrey, Zipf (AT); Armin Schoisswohl, Wels (AT)

(73) Assignee: General Electric Company, Schenectady, NY (US)

( * ) Notice: Subject to any disclaimer, the term of this patent is extended or adjusted under 35 U.S.C. 154(b) by 300 days.

(21) Appl. No.: 13/104,486

(22) Filed: May 10, 2011

(65) Prior Publication Data

US 2012/0288172 A1 Nov. 15, 2012

(51) Int. Cl.
*G06K 9/00* (2006.01)

(52) U.S. Cl.
USPC ........... 382/128; 382/131; 382/132; 600/407; 600/437; 600/441; 128/916; 128/922

(58) Field of Classification Search
USPC .................................................. 382/128–131
See application file for complete search history.

(56) References Cited

U.S. PATENT DOCUMENTS

| | | | | |
|---|---|---|---|---|
| 5,538,003 A * | 7/1996 | Gadonniex et al. | ........... | 600/445 |
| 5,967,987 A * | 10/1999 | Sumanaweera et al. | ...... | 600/454 |
| 5,997,480 A * | 12/1999 | Sumanaweera et al. | ...... | 600/454 |
| 6,322,509 B1 * | 11/2001 | Pan et al. | ........... | 600/443 |
| 7,090,640 B2 * | 8/2006 | Barth et al. | ........... | 600/443 |
| 7,110,583 B2 * | 9/2006 | Yamauchi | ........... | 382/128 |
| 7,428,334 B2 * | 9/2008 | Schoisswohl et al. | ........ | 382/173 |
| 7,450,746 B2 * | 11/2008 | Yang et al. | ........... | 382/128 |
| 7,454,048 B2 * | 11/2008 | Schoisswohl et al. | ........ | 382/131 |
| 7,507,204 B2 * | 3/2009 | Shim et al. | ........... | 600/443 |
| 7,558,402 B2 * | 7/2009 | Zhou et al. | ........... | 382/103 |
| 7,794,398 B2 * | 9/2010 | Salgo | ........... | 600/443 |
| 7,853,304 B2 * | 12/2010 | Bauman et al. | ........... | 600/407 |
| 7,853,310 B2 * | 12/2010 | Vining et al. | ........... | 600/425 |
| 7,940,966 B2 * | 5/2011 | Yu et al. | ........... | 382/128 |
| 8,047,992 B2 * | 11/2011 | Hashimoto et al. | ........... | 600/443 |
| 8,184,882 B2 * | 5/2012 | Yu et al. | ........... | 382/128 |
| 2004/0127794 A1 * | 7/2004 | Murashita | ........... | 600/442 |
| 2005/0033123 A1 * | 2/2005 | Gardner et al. | ........... | 600/300 |
| 2005/0281444 A1 * | 12/2005 | Lundberg et al. | ........... | 382/128 |
| 2006/0004291 A1 * | 1/2006 | Heimdal et al. | ........... | 600/459 |
| 2006/0056672 A1 | 3/2006 | Barth et al. | | |
| 2006/0056690 A1 * | 3/2006 | Schoisswohl et al. | ........ | 382/173 |
| 2006/0291705 A1 * | 12/2006 | Baumann et al. | ........... | 382/128 |
| 2007/0016019 A1 * | 1/2007 | Salgo | ........... | 600/437 |
| 2007/0027528 A1 * | 2/2007 | Agnew | ........... | 623/1.24 |
| 2007/0167699 A1 * | 7/2007 | Lathuiliere et al. | ........... | 600/407 |
| 2007/0232908 A1 * | 10/2007 | Wang et al. | ........... | 600/437 |
| 2007/0276254 A1 * | 11/2007 | Yang et al. | ........... | 600/463 |
| 2008/0117210 A1 * | 5/2008 | Razeto et al. | ........... | 345/424 |
| 2008/0226148 A1 * | 9/2008 | Gu et al. | ........... | 382/128 |
| 2009/0060306 A1 * | 3/2009 | Ohuchi et al. | ........... | 382/131 |
| 2010/0040200 A1 * | 2/2010 | Ema et al. | ........... | 378/98.12 |

(Continued)

*Primary Examiner* — Jayesh A Patel
*Assistant Examiner* — Iman K Kholdebarin

(57) ABSTRACT

An method and system for ultrasound imaging includes accessing a first cross-plane image of a first plane. The method and system includes identifying a first region including a structure in the first cross-plane image. The method and system includes accessing a second cross-plane image of a second plane, where the second plane intersects the first plane. The method and system includes identifying a second region including the structure in the second cross-plane image. The method and system includes automatically configuring acquisition parameters based on at least one of the first region and the second region. The method and system includes implementing the acquisition parameters to acquire data of the structure. The method and system includes generating an image from the data and displaying the image.

19 Claims, 5 Drawing Sheets

(56) References Cited

U.S. PATENT DOCUMENTS

| | | | |
|---|---|---|---|
| 2010/0130855 A1* | 5/2010 | Lundberg et al. | 600/437 |
| 2010/0160783 A1* | 6/2010 | Halmann et al. | 600/447 |
| 2011/0255762 A1* | 10/2011 | Deischinger et al. | 382/131 |
| 2011/0257529 A1* | 10/2011 | Casciaro et al. | 600/443 |
| 2012/0014588 A1* | 1/2012 | Chono | 382/133 |
| 2012/0130245 A1* | 5/2012 | Chono | 600/443 |
| 2012/0232392 A1* | 9/2012 | Tanabe et al. | 600/443 |
| 2012/0288172 A1* | 11/2012 | Perrey et al. | 382/131 |
| 2013/0158403 A1* | 6/2013 | Gottschalk et al. | 600/447 |

* cited by examiner

METHOD AND SYSTEM FOR ULTRASOUND IMAGING WITH CROSS-PLANE IMAGES

FIELD OF THE INVENTION

This disclosure relates generally to method and system for using cross-plane images to automatically configure acquisition parameters for future data acquisition.

BACKGROUND OF THE INVENTION

In medical imaging, a region-of-interest (ROI) is typically used to denote a region, which can be one-dimensional, two-dimensional or three-dimensional, from which data is acquired. The data is then, in turn, used to generate one or more images. It is critical to select a ROI of the appropriate size and location in order to acquire images that are as clinically relevant as possible.

The ROI needs to be large enough and in the right location to cover the complete structure being investigated. However, the ROI should not be larger than needed in order to maximize resolution. For imaging modalities capable of displaying a live image, such as ultrasound, having a smaller ROI will help to ensure that the maximum achievable frame rate of the live image is realized. An ROI that is larger than necessary will result in a reduced frame rate. Additionally, having too large of an ROI may also result in lower spatial resolution, which may lead to images which are not as clinically useful.

Again, using conventional ultrasound as an example, it is typically desired to center the object being imaged in a field-of-view (FOV) of the probe. According to conventional techniques, the user acquires a two-dimensional image and then determines the ROI based on this two-dimensional image. However, since the two-dimensional image typically does not include any elevational information, it is impossible for the user to know if the ROI is appropriately placed. Additionally, it is difficult for the user to determine if the object is centered within the field-of-view of the probe since the user has only a two-dimensional image for reference.

For these and other reasons, there is a need for an improved method and system for medical imaging.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes accessing a first cross-plane image of a first plane. The method includes identifying a first region including a structure in the first cross-plane image. The method includes accessing a second cross-plane image of a second plane, where the second plane intersects the first plane. The method includes identifying a second region including the structure in the second cross-plane image. The method includes automatically configuring acquisition parameters based on at least one of the first region and the second region. The method includes implementing the acquisition parameters to acquire data of the structure. The method includes generating an image from the data and displaying the image.

In another embodiment, a method of medical imaging includes accessing a first cross-plane image of a first plane and accessing a second cross-plane image of a second plane, where the second plane intersects the first plane. The method includes identifying a first contour of a structure in the first cross-plane image and identifying a second contour of the structure in the second cross-plane image. The method includes automatically calculating size data and position data for the structure based on the first contour and the second contour. The method includes automatically positioning a 3D region-of interest (ROI) around the structure using the size data and the position data. The method includes acquiring volumetric data of the 3D region-of-interest (ROI), generating an image from the volumetric data and displaying the image.

In another embodiment, an ultrasound imaging system includes a probe adapted to scan a volume of interest, a display device and a processor in electronic communication with the probe and the display device. The processor is configured to control the probe to acquire a first cross-plane image of a first plane and a second cross-plane image of a second plane. The processor is configured to implement a segmentation algorithm on the first cross-plane image to identify a first contour of a structure. The processor is configured to implement a segmentation algorithm on the second cross-plane image to identify a second contour of the structure. The processor is configured to automatically configure acquisition parameters based on at least one of the first contour and the second contour. The processor is configured to implement the acquisition parameters to acquire data of the structure. The processor is configured to generate an image from the data and display the image on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
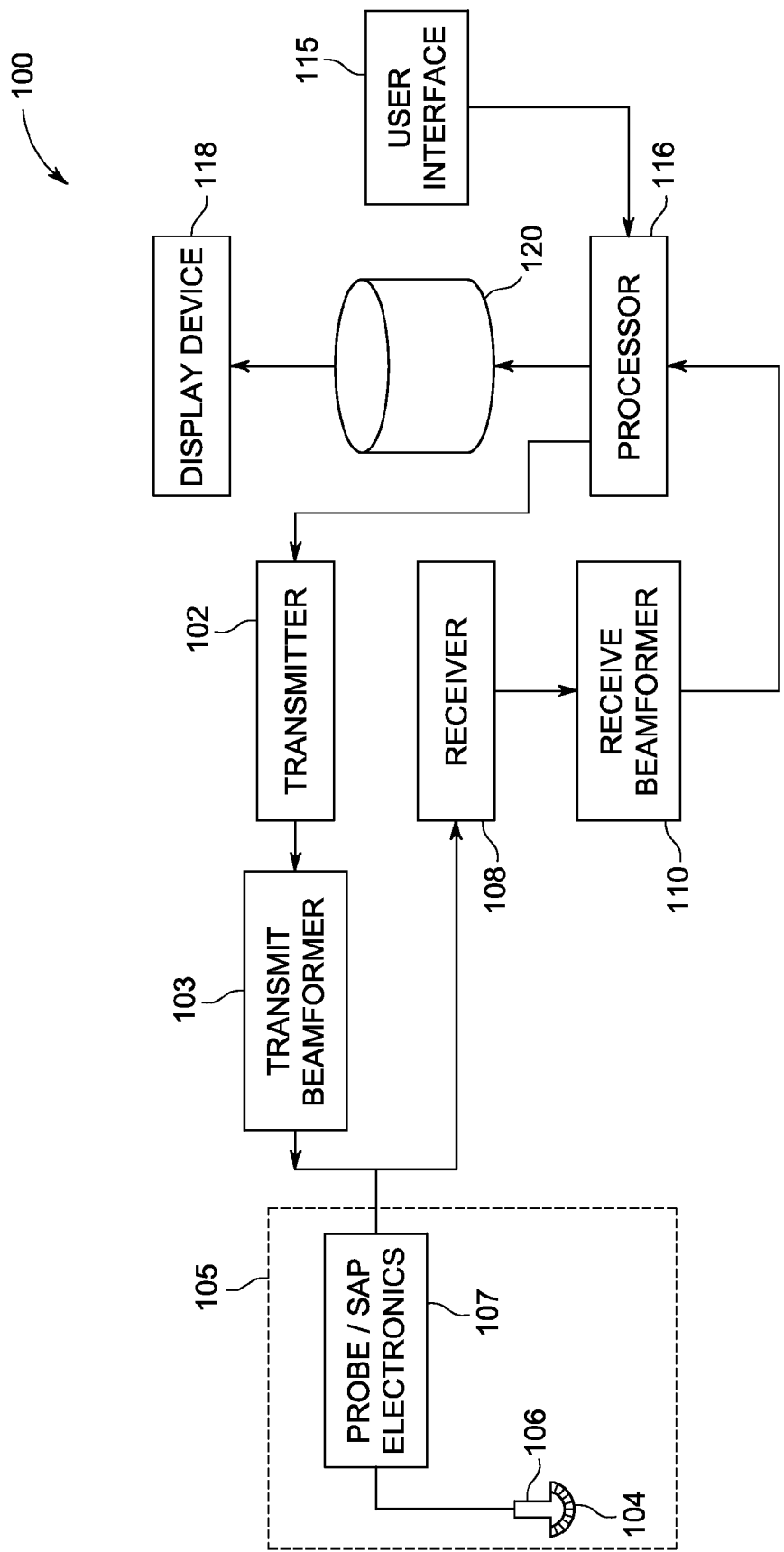
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmitter 102 that transmits a signal to a transmit beamformer 103 which in turn drives transducer elements 104 within a transducer array 106 to emit pulsed ultrasonic signals into a structure, such as a patient (not shown). A probe 105 includes the transducer array 106, the transducer elements 104 and probe/SAP electronics 107. The probe/SAP electronics 107 may be used to control the switching of the transducer elements 104. The probe/SAP electronics 107 may also be used to group the transducer elements 104 into one or more sub-apertures. A variety of geometries of transducer arrays may be used. The pulsed ultrasonic signals are back-scattered from structures in the body, like blood cells or muscular tissue, to produce echoes that return to the transducer elements 104. The echoes are converted into electrical signals, or ultrasound data, by the transducer elements 104 and the electrical signals are received by a receiver 108. For purposes of this disclosure, the term ultrasound data may include data that was acquired and/or processed by an ultrasound system. The electrical signals representing the received echoes are passed through a receive beamformer 110 that outputs ultrasound data. A user interface 115 may be used to control operation of the ultrasound imaging system 100, including, to control the input of patient data, to change a scanning or display parameter, and the like.

The ultrasound imaging system 100 also includes a processor 116 to process the ultrasound data and generate frames or images for display on a display device 118. The processor 116 may be adapted to perform one or more processing operations according to a plurality of selectable ultrasound modalities on the ultrasound data. Other embodiments may use multiple processors to perform various processing tasks. The processor 116 may also be adapted to control the acquisition of ultrasound data with the probe 105. The ultrasound data may be processed in real-time during a scanning session as the echo signals are received. For purposes of this disclosure, the term "real-time" is defined to include a process performed with no intentional lag or delay. An embodiment may update the displayed ultrasound image at a rate of more than 20 times per second. The images may be displayed as part of a live image. For purposes of this disclosure, the term "live image" is defined to include a dynamic image that updates as additional frames of ultrasound data are acquired. For example, ultrasound data may be acquired even as images are being generated based on previously acquired data while a live image is being displayed. Then, according to an embodiment, as additional ultrasound data are acquired, additional frames or images generated from more-recently acquired ultrasound data are sequentially displayed. Additionally or alternatively, the ultrasound data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the ultrasound signal while a second processor may be used to further process the data prior to displaying an image.

Still referring to FIG. 1, the ultrasound imaging system 100 may continuously acquire ultrasound data at a frame rate of, for example, 20 Hz to 150 Hz. However, other embodiments may acquire ultrasound data at a different rate. A memory 120 is included for storing processed frames of acquired ultrasound data that are not scheduled to be displayed immediately. In an exemplary embodiment, the memory 120 is of sufficient capacity to store at least several seconds worth of frames of ultrasound data. The frames of ultrasound data are stored in a manner to facilitate retrieval thereof according to its order or time of acquisition. As described hereinabove, the ultrasound data may be retrieved during the generation and display of a live image. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring ultrasound data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well known by those skilled in the art and will therefore not be described in further detail.

In various embodiments of the present invention, ultrasound data may be processed by other or different mode-related modules (e.g., B-mode, Color Doppler, power Doppler, M-mode, spectral Doppler, anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed. The ultrasound imaging system 100 may be configured as a console system, a cart-based system, or a portable system, such as a hand-held or laptop-style system.

Figure 2:
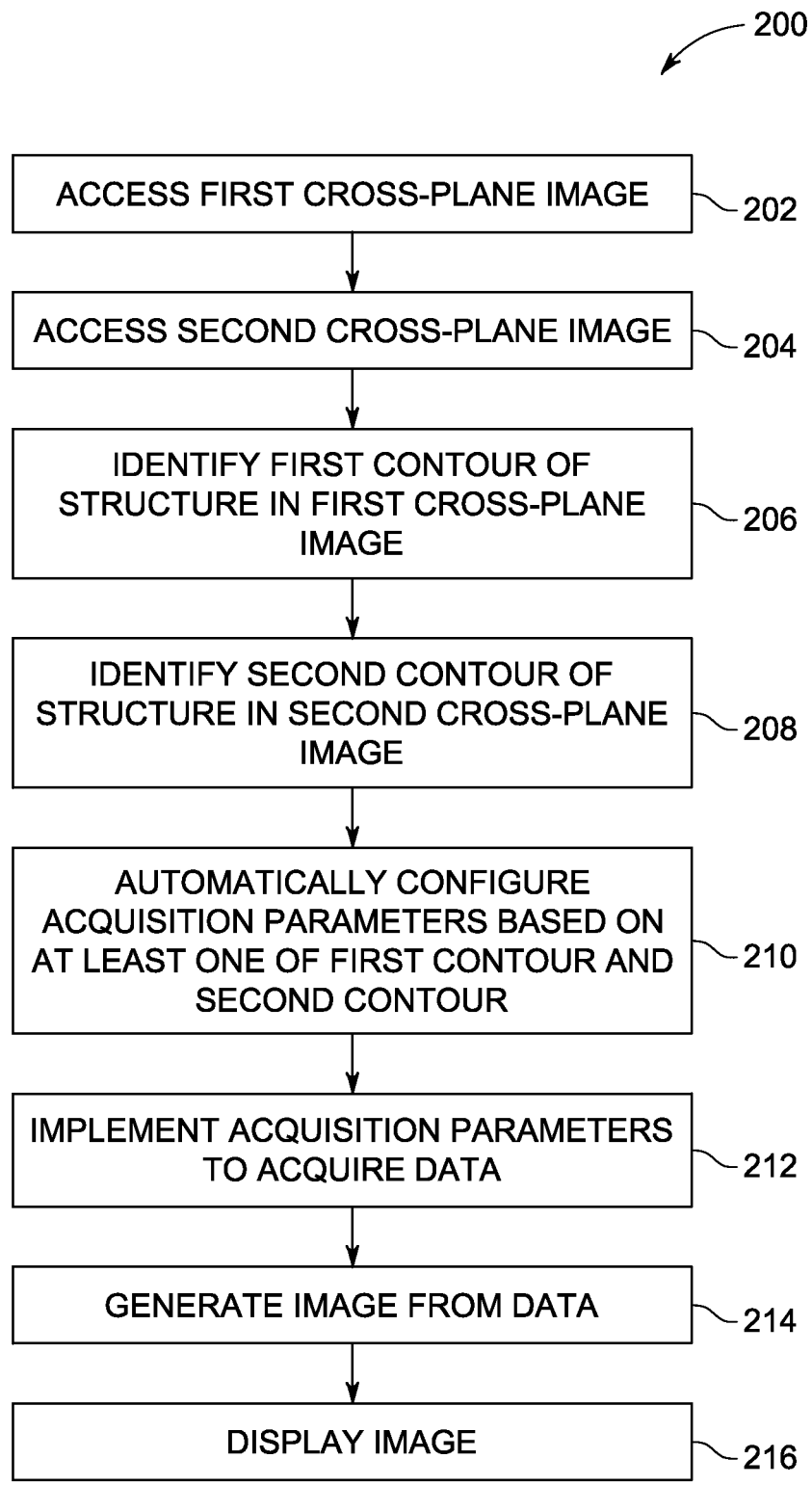
FIG. 2 is a flow chart illustrating a method in accordance with an embodiment.

FIG. 2 is a flow chart illustrating a method 200 in accordance with an embodiment. The individual blocks represent steps that may be performed in accordance with the method 200. The technical effect of the method 200 is the display of an image generated from data acquired based on the implementation of automatically configured acquisition parameters. The steps of the method 200 will be described according to an exemplary embodiment where the steps are performed with the ultrasound imaging system 100 (shown in FIG. 1).

Figure 3:
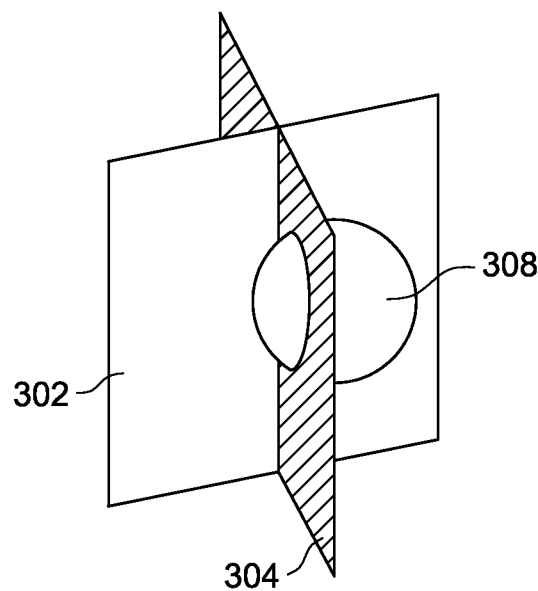
FIG. 3 is a schematic representation of a first plane and a second plane intersecting a structure in accordance with an embodiment.

FIG. 3 is a schematic representation of a first plane 302 and a second plane 304 intersecting a structure 308 in accordance with an embodiment. According to an embodiment, data acquired of the first plane 302 may be displayed as a first cross-plane image and data acquired of the second plane 304 may be displayed as a second cross-plane image. First and second cross-plane images will be described in detail hereinafter.

Figure 4:
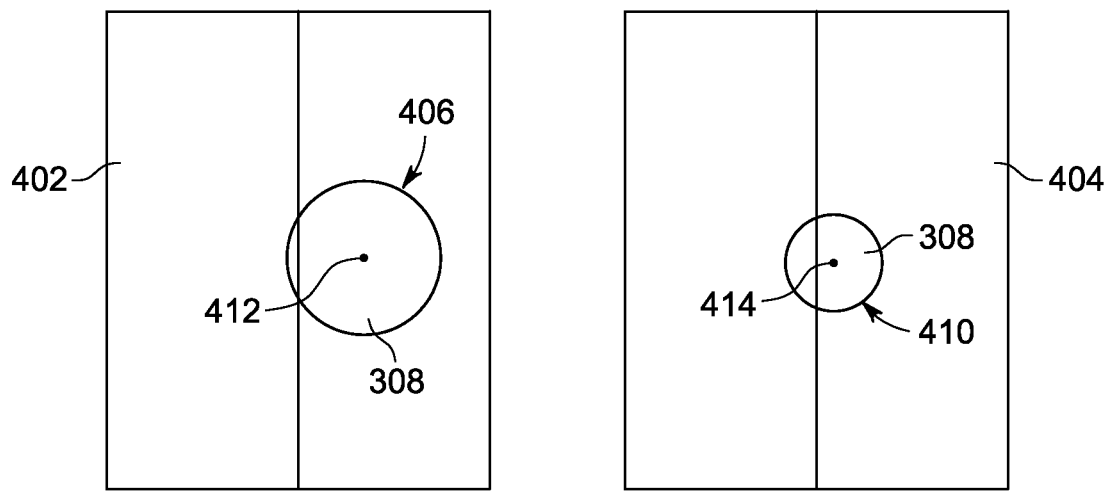
FIG. 4 is a schematic representation of a first cross-plane image and a second cross-plane image in accordance with an embodiment.

FIG. 4 is a schematic representation of a first cross-plane image 402 and a second cross-plane image 404. According to an exemplary embodiment, the first cross-plane image 402 represents an image of the first plane 302 (shown in FIG. 3) and the second cross-plane image 404 represents an image of the second plane 304 (shown in FIG. 3). A common reference number is used to identify the structure 308 in both FIG. 3 and FIG. 4 in accordance with an embodiment.

Referring now to FIGS. 1, 2, and 4, at step 202, the processor 116 accesses a first cross-plane image, such as the first cross-plane image 402. At step 204, the processor 116 accesses a second cross-plane image, such as the second cross-plane image 404. As described previously, the first cross-plane image 402 may be of the first plane 302 (shown in FIG. 3) and the second cross-plane image 404 may be of the second plane 304 (shown in FIG. 3). According to an embodiment, the processor 116 may first control the acquisition of data in order to generate the first cross-plane image 402 and the second cross-plane image 404 before step 202 of the method 200. According to other embodiments, the processor 116 may retrieve the first and second cross-plane images (402, 404) from a storage device such as memory 120 or from a remotely located storage device, such as a picture archiving and communications system (not shown) during step 202.

At step 206 of the method 200, the processor 116 identifies a first contour 406 of the structure 308 in the first cross-plane image 402. At step 208, the processor 116 identifies a second contour 410 of the structure 308 in the second cross-plane image 404. The processor 116 may use an object recognition algorithm in order to identify the first contour 406 and the second contour 410. For example, according to an exemplary embodiment where the processor 116 is trying to identify a generally spherical object, the processor 116 may implement an object recognition algorithm adapted to identify a generally circular contour, since all cross sections of a sphere are circular. Other embodiments may be adapted to identify structures with shapes other than spherical.

At step 210, the processor 116 automatically configures acquisition parameters based on one or both of the first contour 406 and the second contour 410. For purposes of this disclosure, the term "acquisition parameters" is defined to include settings that control a region from which data is acquired. According to an exemplary embodiment, the acquisition parameters are the settings that control the ultrasound data that will be acquired by the probe 105. The acquisition parameters control the ultrasound beams, which in turn control the portions of a patient's anatomy that are imaged. For example, the acquisition parameters will control the position of the plane that is acquired when acquiring two-dimensional ultrasound data and the acquisition parameters will control the position and size of the volume that is acquired when acquiring volumetric ultrasound data. Non-limiting examples of acquisition parameters include: beam depth, beam steering angles, beam width, and beam spacing. For example, according to an embodiment, it may be desirable to acquire two additional cross-plane images, where each of the additional cross-plane images are centered through the structure 308. The processor 116 may, for example, determine a first center of mass 412 of the structure 308 based on the first contour 406 and a second center of mass 414 of the structure 308 based on the second contour 410. According to an embodiment where the first contour 308 and the second contour 410 are both generally circular, calculating the center of mass may include identifying the center of each generally circular contour. The processor 116 may then configure acquisition parameters to enable the acquisition of additional two-dimensional data for planes that pass through the first center of mass 412 and the second center of mass 414 respectively in order to center the structure within a field-of-view of the probe.

Next, at step 212, the processor 116 implements the acquisition parameters from step 210 and acquires data. For example, according to an exemplary embodiment, the processor 116 may implement the acquisition parameters to acquire two-dimensional data for a third plane that passes through the first center of mass 412. The third plane may be parallel to the second plane 404 according to an embodiment. The processor 116 may also implement the acquisition parameters to acquire fourth two-dimensional data for a fourth plane through the second center of mass 414. The fourth plane may be parallel to the first plane 402 according to an embodiment.

At step 214, the processor 116 generates one or more images from the data. For example, the processor 116 may generate a third image based on the data for the third plane and the processor 116 may generate a fourth image based on the data for the fourth plane. Then, at step 216, the processor 116 displays the images on the display device 118. According to another embodiment, the steps 212, 214, and 216 may be repeated multiple times in order to generate and display multiple frames of a live or dynamic image.

According to another embodiment, the steps 202, 204, 206, 208, 210, 212, 214, and 216 may be repeated multiple times. This may be particularly useful when acquiring live or dynamic ultrasound images. According to one such embodiment, the processor 116 may identify a contour in each of the cross-plane images each iteration before automatically configuring the acquisition parameters and enabling the acquisition of additional data based on the contours. This technique ensures that the user's live image is not corrupted due to any relative movement that occurs once the scanning has started.

The method 200 shows an embodiment where a contour is identified in each of two cross-plane images. However, according to other embodiments, the structure may be identified through techniques other than identifying a contour. For example, a user may identify a region including a structure in one or more cross-plane images according to other embodiments. For example, the user may place a region-of-interest (ROI) around the structure in one or more cross-plane images. The ROI is used to identify a particular region in a two-dimensional image. According to an embodiment, the ROI may include a rectangle that is adjustable for position as well as length and width by the user. By positioning the ROI over a portion of the image, such as a particular structure, the user is able to easily identify a structure in an image.

Figure 5:
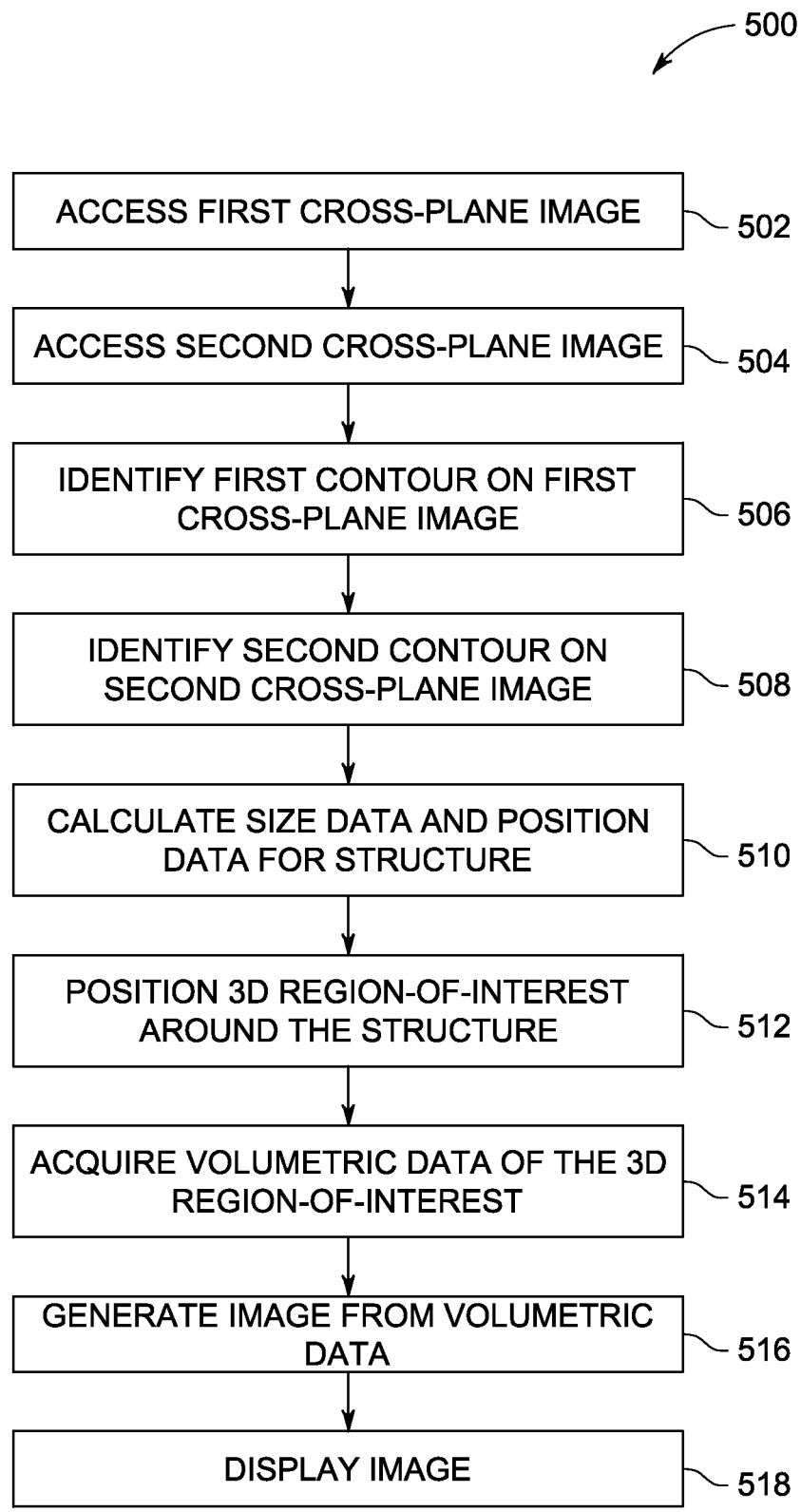
FIG. 5 is a flow chart illustrating a method in accordance with an embodiment.

FIG. 5 is a flow chart illustrating a method 500 in accordance with an embodiment. The individual blocks represent steps that may be performed in accordance with the method 500. The technical effect of the method 500 is display of an image generated from volumetric data acquired based on the implementation of automatically configured acquisition parameters. The steps of the method 500 will be described according to an exemplary embodiment where the steps are performed with the ultrasound imaging system 100 (shown in FIG. 1). However, it should be appreciated that the method 500 may be performed by ultrasound imaging systems with different configurations than the one shown in FIG. 1.

Figure 6:
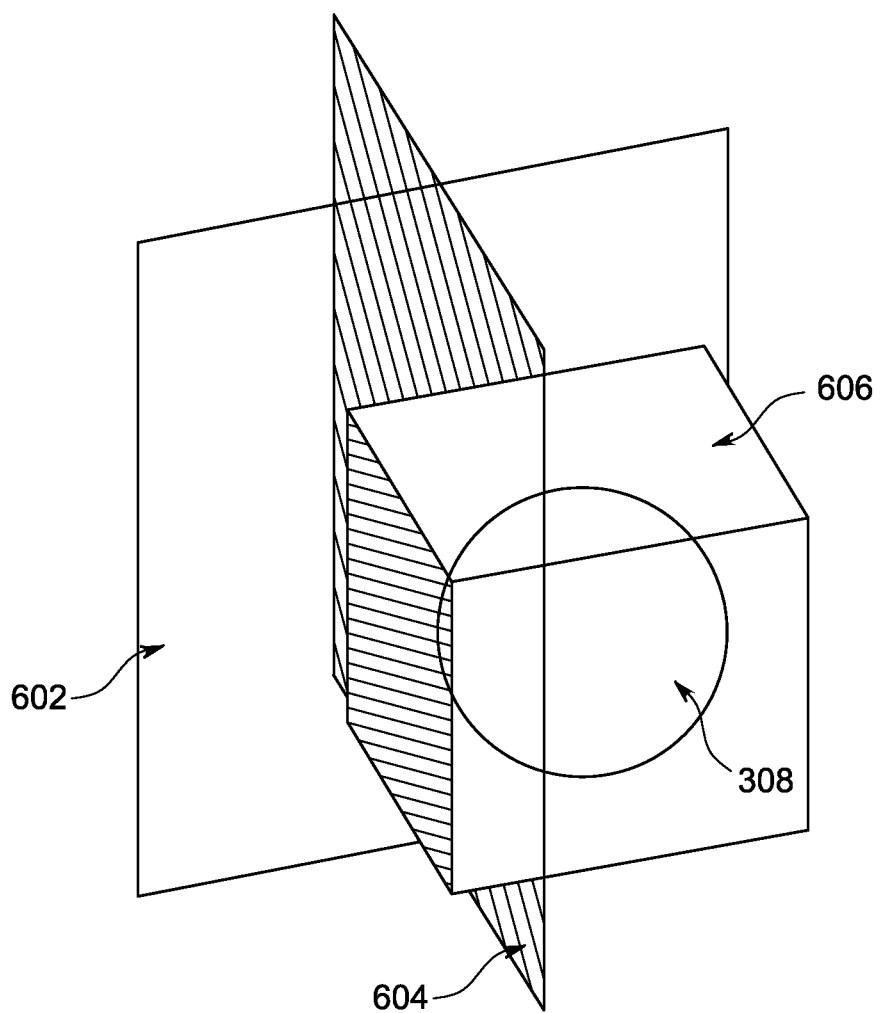
FIG. 6 is a schematic representation of a first plane, a second plane and a 3D region-of-interest shown with respect to a structure in accordance with an embodiment.

FIG. 6 is a schematic representation of a first plane 602, a second plane 604 and a 3D region-of-interest (ROI) 606 shown with respect to the structure 308 in accordance with an embodiment. A common reference number is used to identify the structure 308 in FIGS. 3, 4 and, 6 in accordance with an embodiment.

Referring to FIGS. 1, 5 and 6, at step 502, the processor 116 accesses a first cross-plane image. At step 504, the processor 116 accesses a second cross-plane image. The first cross-plane image may be of the first plane 602 and the second cross-plane image may be of the second plane 604. The processor 116 may first control the acquisition of data in order to generate the first cross-plane image and the second cross-plane image before step 502 of the method 500. According to other embodiments, the processor 116 may retrieve the first and second cross-plane images from a storage device such as memory 120 or from a remotely located storage device, such as a picture archiving and communications system (not shown).

At step 506, the processor 116 identifies a first contour on the first cross-plane image. At step 508, the processor 116 identifies a second contour on the second cross-plane image.

The processor 116 may use an object recognition algorithm in order to identify the first contour and the second contour of the structure 308 in a manner similar to that previously described with respect to steps 206 and 208 of the method 200 (shown in FIG. 2). For example, referring to FIG. 4, the processor 116 may identify the first contour 406 in the first cross-plane image 402 and the second contour 410 in the second cross-plane image 404.

Referring to FIGS. 1, 4, and 5, at step 510, the processor 116 calculates size data and position data for the structure 308. In an exemplary embodiment, the structure 308 is assumed to be generally spherical in shape. As such, the processor 116 may use the first contour 406 and the second contour 410 to calculate both size data and position data for the structure. The processor may first calculate a first center of mass 412 of the first contour 406 and a second center of mass 414 for the second contour 410. The processor 116 may then calculate the position data based on the first center of mass 412 and the second center of mass 414. For example, assuming that the structure 308 is generally spherical, the processor 116 may used the information regarding the first center of mass 412, the second center of mass 414, and the relative locations of the first plane 602 and the second plane 604 in order to calculate position data for the structure 308, such as the three-dimensional location of the center of the structure 308. Then, using the diameters of the first contour 406 and the second contour 410, the processor may calculate size data for the structure 308, such as the a diameter of the structure 308. Again, by assuming the structure 308 is generally spherical, the processor 116 can calculate an overall size of the structure 308 since the relative positioning of the first plane 602 and the second plane 604 are known.

Referring to FIGS. 1, 5, and 6, at step 512, the processor 116 positions a 3D region-of-interest (ROI), such as the 3D ROI 606, around the structure 308 using the size data and the position data calculated during step 510. FIG. 6 includes a schematic representation of a 3D ROI positioned around the structure 308 according to an exemplary embodiment. As described previously, the processor 116 calculated both position data and size data for the structure 308 shown in FIG. 6. The processor 116 may use the position data and the size data to automatically place a 3D ROI around the structure 308. For example, it may be beneficial for a user to view the structure 308 in higher spatial or temporal resolution in order to discern additional details. The placement of the 3D ROI 606 determines the volume from which volumetric data is acquired by the ultrasound imaging system 100. It is desirable to have to smallest possible 3D ROI which still shows all of the desired structure for diagnostic purposes. A small 3D ROI enables one or both of increased spatial resolution and increased temporal resolution for any images generated based from the volumetric data from within the 3D ROI. The embodiment in FIG. 6 shows the 3D ROI 606 as generally box-like in shape. According to an embodiment, it may be desirable to have the dimensions of the 3D ROI 606 exceed the dimensions of the structure 308 by 10% or less. In other words, it may be beneficial for the length, width, and height, of the 3D ROI 606 to exceed the length, width, and height of the structure 308 by less than 10%. Other embodiments may have the 3D ROI exceed the dimensions of the structure by a larger amount, but it may not be possible to acquire and display images with as high of a frame-rate. It should be appreciated that additional embodiments may use a 3D ROI with a shape other than box-like. There may be advantages in terms of frame rate and spatial resolution in using a 3D ROI that conforms more closely to the shape of the structure 308 than a box-shaped 3D ROI such as the 3D ROI 606. For example, for some applications, it may be advantageous to use a 3D ROI with a generally spherical shape.

It is generally desirable to center the field-of-view around the structure 308 for optimal imaging. That is, it is usually best to have the structure in the middle of the probe's field-of-view. The processor 116 may use the contours identified in both of the cross-plane images to determine if the structure is completely within the probe's field-of-view. If a portion of the structure is outside of the field-of-view, the contour will be an open shape instead of a closed shape. According to an embodiment, the processor 116 may communicate a warning to the user, such as an audible signal, a warning light, a text display, and the like, if one or both of the contours indicate that the structure 308 is outside of the field-of-view. Additionally, the processor 116 may communicate instructions to the user for repositioning the probe 105 in order to include all of the structure 308 within the field-of-view.

Referring back to FIG. 5, at step 514, the processor 116 acquires volumetric data of the 3D ROI 606 (shown in FIG. 6) that was automatically positioned by the processor 116 during step 512. In order to acquire volumetric data of the 3D ROI, the processor 116 configures acquisition parameters in order to facilitate the acquisition of volumetric data of the 3D ROI 606. As described hereinabove, the acquisition parameters may include beam depth, beam steering angles, beam width, and beam spacing. For modalities other than ultrasound, the acquisition parameters still control the specific portion of the patient's anatomy for which data is collected. Next, at step 516, the processor 116 generates an image from the volumetric data. For example, the image may include a two-dimensional image showing a slice through the structure, or the processor 116 may generate another type of image such as a volume-rendered image. At step 518, the processor 116 displays the image on the display device 118.

According to embodiments, the steps 514, 516, and 518 may be repeated multiple times to facilitate the generation and display of a live image from volumetric data. According to other embodiments, steps 502 and 504 may be replaced with steps where live cross-plane images are acquired and displayed in real-time. The processor 116 (shown in FIG. 1) would then use one or more image frames from the live cross-plane images in order to identify the contours of the structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:
1. A method of ultrasound imaging comprising:
accessing a first cross-plane image of a first plane;
identifying a first region including a structure in the first cross-plane image,
wherein said identifying the first region comprises implementing a segmentation algorithm to identify a contour of the structure;
accessing a second cross-plane image of a second plane, where the second plane intersects the first plane;

identifying a second region including the structure in the second cross-plane image;
automatically configuring acquisition parameters based on at least one of the first region and the second region, wherein said automatically configuring the acquisition parameters comprises calculating a center of mass of the structure in the first cross-plane image based on the contour;
implementing the acquisition parameters to acquire data of the structure;
generating an image from the data; and
displaying the image.

2. The method of claim 1, wherein said implementing the acquisition parameters comprises acquiring two-dimensional data through the center of mass, where the two-dimensional data is parallel to the second plane.

3. The method of claim 1, wherein said automatically configuring the acquisition parameters comprises automatically configuring the acquisition parameters based on both the first region and the second region.

4. The method of claim 1, wherein said implementing the acquisition parameters comprises implementing the acquisition parameters to acquire volumetric data of the structure.

5. A method of ultrasound imaging comprising:
accessing a first cross-plane image of a first plane;
accessing a second cross-plane image of a second plane, where the second plane intersects the first plane;
identifying a first contour of a structure in the first cross-plane image;
identifying a second contour of the structure in the second cross-plane image;
automatically calculating size data and position data for the structure based on the first contour and the second contour, wherein said automatically calculating the position data comprises calculating a 3D location of a center of the structure based on both the first contour and the second contour;
automatically positioning a 3D region-of-interest (ROI) around the structure using the size data and the position data;
acquiring volumetric data of the 3D region-of-interest (ROI) after said automatically position the 3D region-of-interest (ROI) around the structure;
generating an image from the volumetric data; and
displaying the image.

6. The method of claim 5, wherein said identifying the first contour comprises implementing an algorithm to automatically identify the first contour.

7. The method of ultrasound imaging of claim 5, wherein the 3D region-of-interest (ROI) does not exceed the size of the structure by more than 10 percent in length, width, or height.

8. The method of claim 5, further comprising automatically providing a warning if either the size data or the position data indicate that the structure is outside of a field-of-view (FOV).

9. The method of claim 8, further comprising automatically providing an indication for how to adjust a position of a probe in order to capture all of the structure within a new field-of-view (FOV).

10. The method of ultrasound imaging of claim 5, wherein said automatically positioning the 3D region-of-interest around the structure comprises centering the 3D region-of-interest on the 3D location of the center of the structure.

11. An ultrasound imaging system comprising:
a probe adapted to scan a volume of interest;
a display device; and
a processor in electronic communication with the probe and the display device, wherein the processor is configured to:
control the probe to acquire a first cross-plane image of a first plane;
control the probe to acquire a second cross-plane image of a second plane;
implement a segmentation algorithm on the first cross-plane image to identify a first contour of a structure;
calculate a first center of mass of the structure based on the first contour;
implement a segmentation algorithm on the second cross-plane image to identify a second contour of the structure;
automatically configure acquisition parameters based on at least one of the first contour and the second contour;
implement the acquisition parameters to acquire data of the structure;
generate an image from the data; and
display the image on the display device.

12. The ultrasound imaging system of claim 11, wherein the processor is further configured to calculate a second center of mass of the structure based on the second contour.

13. The ultrasound imaging system of claim 11, wherein the processor is configured to automatically control the probe in order to implement the acquisition parameters.

14. The ultrasound imaging system of claim 11, wherein the processor is configured to implement the acquisition parameters in order to acquire two-dimensional data.

15. The ultrasound imaging system of claim 11, wherein the processor is configured to automatically configure the acquisition parameters based on both the first contour and the second contour.

16. A method of ultrasound imaging comprising:
accessing a first cross-plane image of a first plane;
identifying a first region including a structure in the first cross-plane image, wherein said identifying the first region comprises implementing a segmentation algorithm to identify a first contour of the structure;
accessing a second cross-plane image of a second plane, where the second plane intersects the first plane;
identifying a second region including the structure in the second cross-plane image, wherein said identifying the second region comprises implementing a segmentation algorithm to identify a second contour of the structure;
calculating a center of the structure based on the first contour and the second contour;
automatically configuring acquisition parameters based on the center of the structure;
implementing the acquisition parameters to acquire data of the structure;
generating an image from the data; and
displaying the image.

17. The method of claim 16, wherein said calculating the center of the structure comprises calculating a location of a 3D center of the structure.

18. The method of claim 16, wherein said calculating the center of the structure comprises calculating a center of mass of the structure in the first cross-plane image.

19. The method of claim 16, wherein said automatically configuring the acquisition parameters based on the center of the structure comprises centering a 3D region-of-interest on the center of the structure.

* * * * *